(12) United States Patent
Bodenmüller et al.

(10) Patent No.: US 11,872,587 B2
(45) Date of Patent: Jan. 16, 2024

(54) CARTRIDGE ASSEMBLY, SLEEVE, SYSTEM AND METHOD OF ASSEMBLING A CARTRIDGE ASSEMBLY

(71) Applicant: Sulzer Mixpac AG, Haag (CH)

(72) Inventors: Tobias Bodenmüller, Haag (CH); Marcel Richter, Haag (CH); Richard Lavelanet, Haag (CH)

(73) Assignee: MEDMIX SWITZERLAND AG, Haag (CH)

( * ) Notice: Subject to any disclaimer, the term of this patent is extended or adjusted under 35 U.S.C. 154(b) by 32 days.

(21) Appl. No.: 17/631,789

(22) PCT Filed: Jul. 28, 2020

(86) PCT No.: PCT/EP2020/071214
§ 371 (c)(1),
(2) Date: Jan. 31, 2022

(87) PCT Pub. No.: WO2021/023571
PCT Pub. Date: Feb. 11, 2021

(65) Prior Publication Data
US 2022/0266291 A1    Aug. 25, 2022

(30) Foreign Application Priority Data

Aug. 2, 2019  (EP) ..................................... 19189791
Nov. 8, 2019  (EP) ..................................... 19208043

(51) Int. Cl.
*B05C 17/005*  (2006.01)
*B65D 83/00*  (2006.01)
(Continued)

(52) U.S. Cl.
CPC .......... *B05C 17/015* (2013.01); *A61C 19/063* (2013.01); *A61F 9/0008* (2013.01);
(Continued)

(58) Field of Classification Search
CPC ............ B05C 17/015; B05C 17/00576; B05C 17/00583; B65D 83/0072; B65D 83/0055;
(Continued)

(56) References Cited

U.S. PATENT DOCUMENTS 4,858,759 A    8/1989  Mauthe et al.
5,323,931 A *  6/1994  Robards, Jr. ........ B05C 17/0123
                                                222/326

(Continued)

FOREIGN PATENT DOCUMENTS

EP    0144925 A2    6/1985
EP    1266844 B1    1/2007
EP    1284163 B1    3/2008

OTHER PUBLICATIONS

International Preliminary Report on Patentability dated Feb. 17, 2022 in corresponding International Application No. PCT/EP2020/071214.

*Primary Examiner* — Frederick C Nicolas
(74) *Attorney, Agent, or Firm* — GLOBAL IP COUNSELORS, LLP

(57) ABSTRACT

A cartridge assembly includes a cartridge and a sleeve, the cartridge having a solid head part and a cartridge wall formed by a film integrally formed with the head part, the cartridge being received in the sleeve.

18 Claims, 5 Drawing Sheets

(51) Int. Cl.
*B05C 17/015* (2006.01)
*A61M 31/00* (2006.01)
*A61C 19/06* (2006.01)
*A61F 9/00* (2006.01)
*B65D 77/06* (2006.01)

(52) U.S. Cl.
CPC ....... *A61M 31/00* (2013.01); *B05C 17/00576* (2013.01); *B05C 17/00583* (2013.01); *B65D 77/06* (2013.01); *B65D 83/005* (2013.01); *B65D 83/0055* (2013.01); *B65D 83/0072* (2013.01); *Y02B 10/30* (2013.01)

(58) Field of Classification Search
CPC ...... B65D 83/005; B65D 77/06; Y02B 10/30; A61C 19/063; A61F 9/0008; A61M 31/00
See application file for complete search history.

(56) References Cited

U.S. PATENT DOCUMENTS

| | | | |
|---|---|---|---|
| 6,206,244 B1 * | 3/2001 | Muhlbauer | B05C 17/00576 |
| | | | 222/105 |
| 6,223,941 B1 | 5/2001 | Nealey | |
| 7,445,135 B2 | 11/2008 | Miyata et al. | |
| 7,905,654 B1 * | 3/2011 | Cordero | B01F 31/445 |
| | | | 366/256 |
| 8,220,668 B2 | 7/2012 | Cadden et al. | |
| 9,688,443 B2 * | 6/2017 | Hanten | B65D 35/28 |
| 9,968,959 B2 | 5/2018 | Frey | |

* cited by examiner

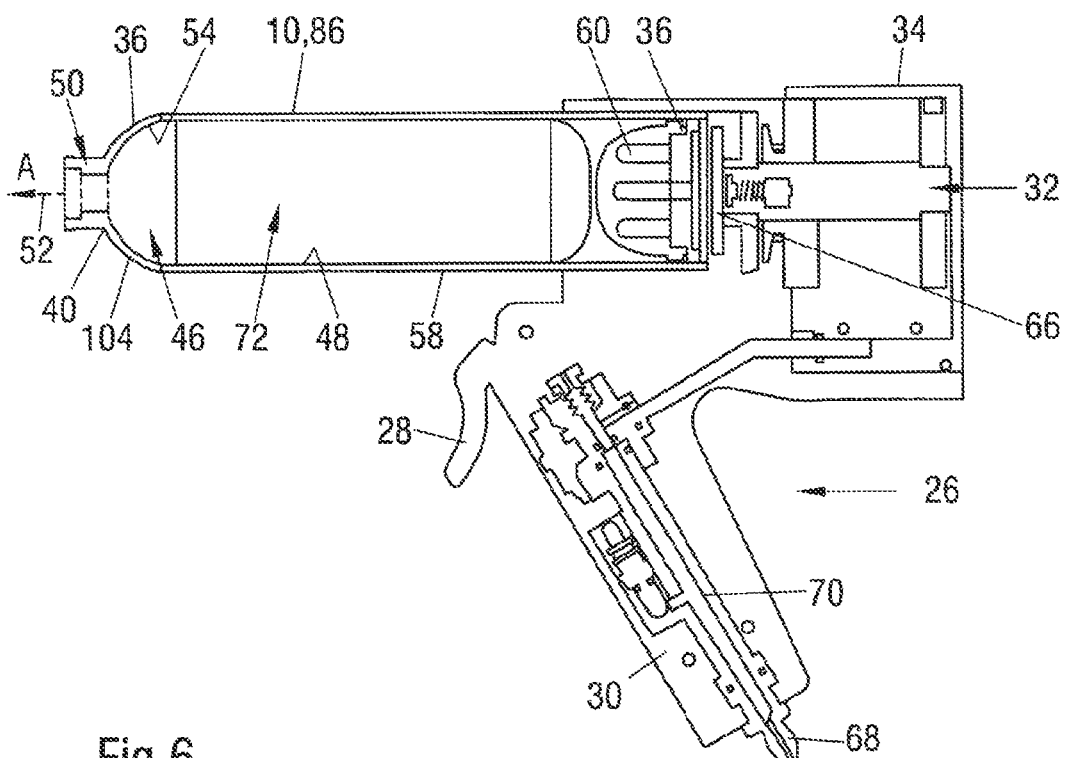
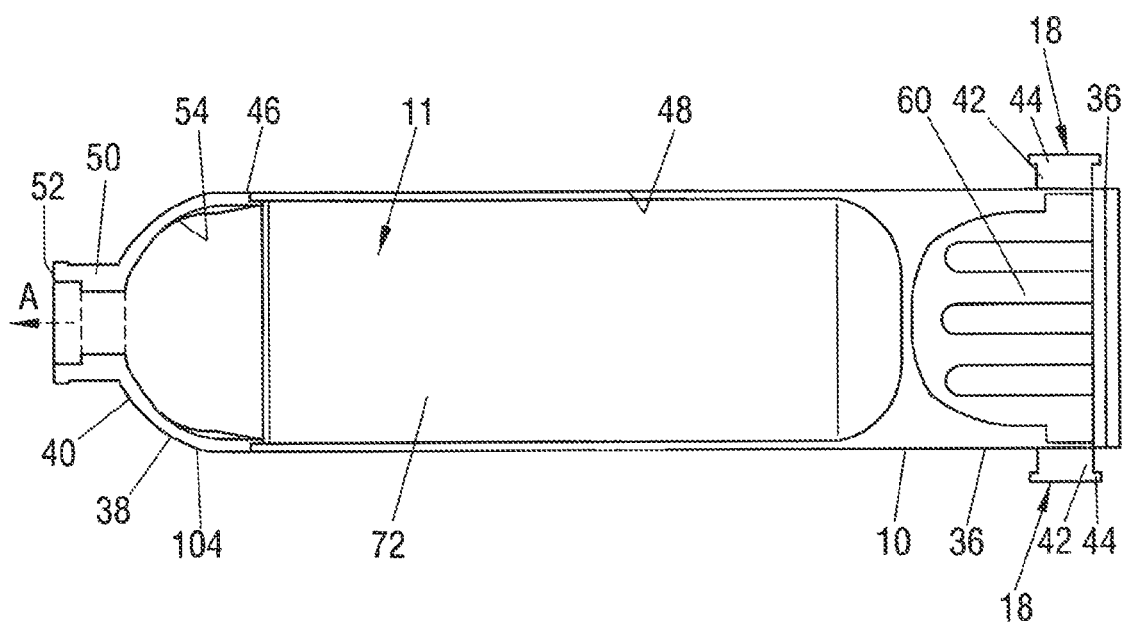

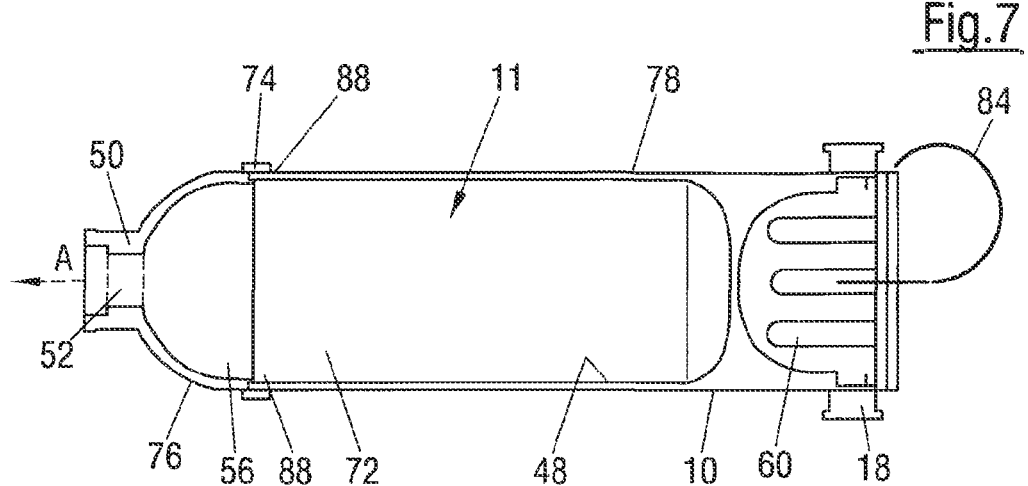
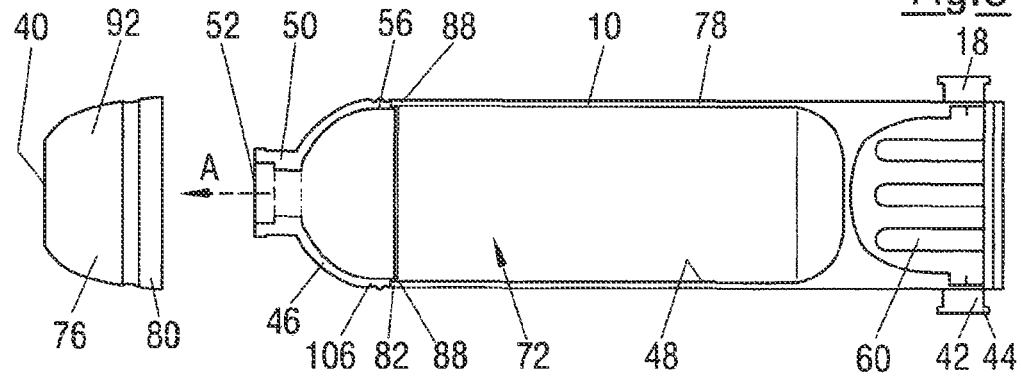
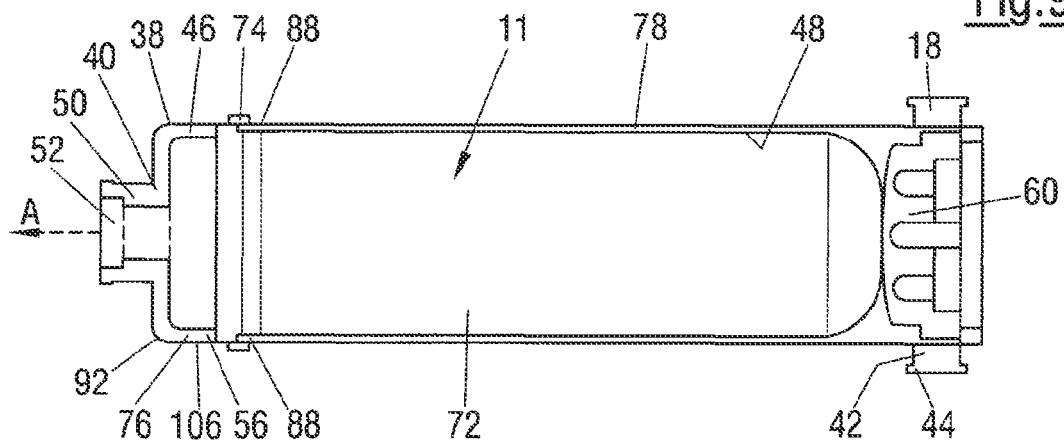

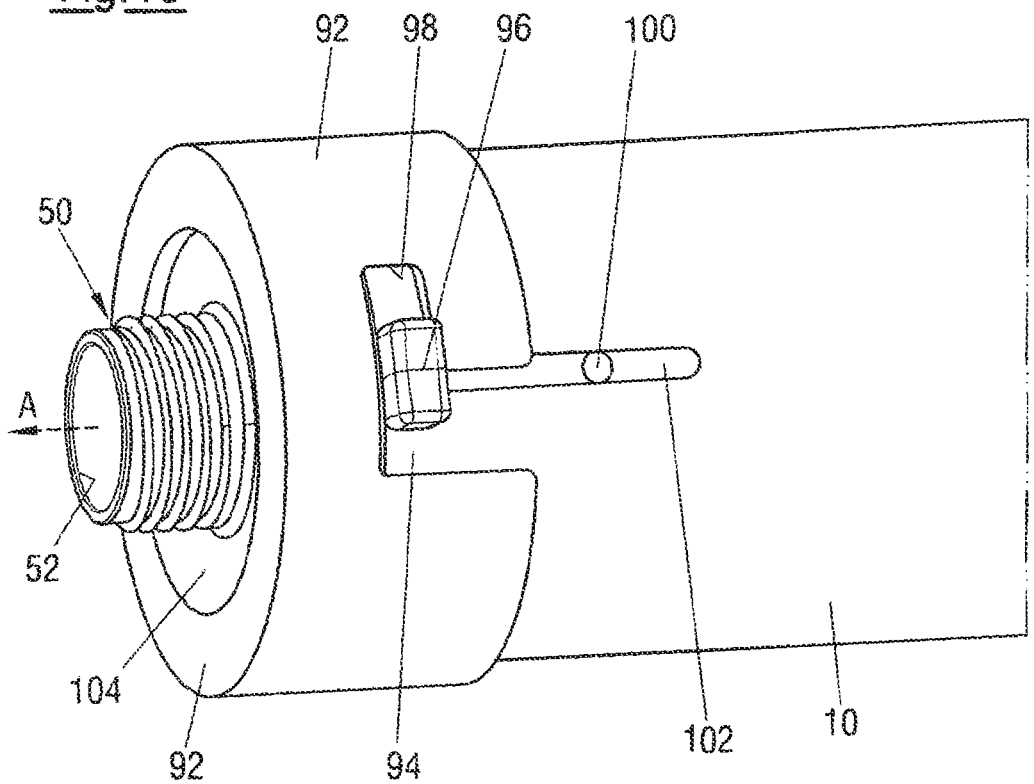
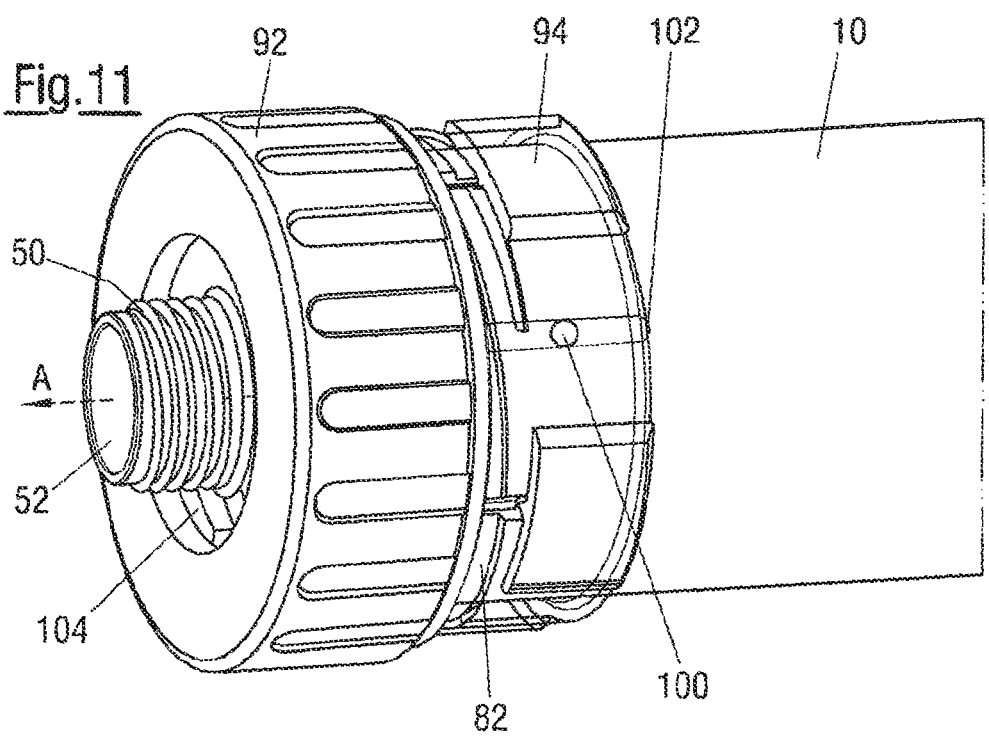

CARTRIDGE ASSEMBLY, SLEEVE, SYSTEM AND METHOD OF ASSEMBLING A CARTRIDGE ASSEMBLY

CROSS-REFERENCE TO RELATED APPLICATION

This application is a U.S. National Stage application of International Application No. PCT/EP2020/071214, filed Jul. 28, 2020, which claims priority to European Patent Application No. 19189791.7, filed Aug. 2, 2019, and European Patent Application No. 19208043.0, Nov. 8, 2019, the contents of each of which are hereby incorporated by reference

BACKGROUND

Field of Invention

The present disclosure relates to a cartridge assembly comprising a cartridge and a sleeve, the cartridge having a solid head part and a cartridge wall formed by a film integrally formed with the head part, the cartridge being received in the sleeve. The disclosure further relates to a sleeve, to a system comprising a dispenser and a cartridge assembly filed with a material and to a method of assembling a cartridge assembly.

Background Information

In the industrial sector, in the aerospace industry, in the construction industry, for example of buildings, and also in the dental sector, conventional cartridges are frequently used to store liquid flowable, frequently pasty or viscous to highly viscous substances and to dispense them for the respective application as required. Examples for such substances are joint sealing compounds, compounds for chemical dowels or chemical anchors, adhesives, pastes or impression materials in the dental sector. These cartridges are usually produced from plastic and are manufactured in an injection molding process.

A distinction is made between single-component systems in which the material to be dispensed is only made of one component and two-component or multicomponent systems in which at least two different components are stored in separate chambers of the same cartridge or in separate cartridges, wherein the components are intimately mixed on dispensing by a dynamic or static mixing apparatus. Examples for this are two-component adhesives or chemical dowels which only harden after the mixing of the two components. Two-component systems are in particular also used in the industrial sector for paints which are often used to generate functional protective layers such as for corrosion protection.

SUMMARY

It has been found that for reasons of environmental protection, film cartridges are increasingly being used. In contrast to regular cartridges which are completely produced from plastic in an injection molding process, at least parts of film cartridges are designed as a film. Usually the cartridge wall bounding the cartridge chamber is made of a film which is connected to a head part made of rigid material, e.g. plastic, comprising the dispensing outlet. This has several advantages. On the one hand, the unfilled film cartridges can be stored and transported in a collapsed state from the cartridge manufacturers to the manufacturers of the filling materials (media) who then take care of the filling of the empty cartridges. Only after being filled the film cartridge is in its expanded state which is comparable in size to a regular non-collapsible cartridge. This means that the necessary space for storage and for transportation can be reduced, since the collapsed cartridges have a reduced size in comparison to regular non-collapsible cartridges.

On the other hand, once the cartridges have been used, i.e. reduced to the collapsed state by dispensing the filling material, the cartridges are significantly reduced in size and weight in comparison to regular cartridges so that the cost of disposal is also reduced. In any case the carbon footprint associated with the film cartridges is reduced in comparison to plastic cartridges that are completely formed in an injection molding process.

Solid cartridges have an inherent stability which film bag cartridges cannot possess, otherwise the film bag cartridge would not collapse on dispensing materials from the cartridge. However, in order to reliably use a film bag cartridge this has to be incorporated into a preferably reusable sleeve which then acts as a support for the film bag cartridge, such an assembly is known as a cartridge assembly.

The sleeve is typically made of metal or of a hard or very hard plastic to ensure that this can be reused. A connection between the dispenser and the cartridge assembly can have to be optimized, on the one hand, to ensure the functionality of the system, and, on the other hand, to ensure that the film bag cartridge can be reliably replaced once the material has been completely dispensed therefrom.

Moreover, in order to ensure a reliable dispensing of materials from the cartridge assembly a piston has to also be inserted into the sleeve. One also has to ensure that the piston is not accidentally discarded on replacing the film bag cartridge in the sleeve.

Prior art cartridges are known from EP0144925A2, U.S. Pat. Nos. 6,223,941B1 and 4,858,759A.

For this reason, it is an object of the disclosure to ensure a reliable connection between a cartridge assembly and a dispenser. It is a further object of the present disclosure to ensure a fast and reliable connection and subsequent release of the cartridge to and from the sleeve. It is a further object to ensure a reliable use of such a cartridge assembly, in particular on the avoidance of a loss of the piston.

This object is satisfied by a cartridge assembly as disclosed herein.

Such a cartridge assembly comprises a film bag cartridge, a sleeve, and a piston, the film bag cartridge having a solid head part and a cartridge wall formed by a film integrally formed with the head part, the film bag cartridge and the piston being received in the sleeve, wherein a part of the sleeve covers a part of the solid head part and the sleeve comprises one or more radial pins that are arranged at an end of the sleeve remote to the head part for connecting the sleeve to a dispenser, wherein the sleeve is of multi-part design.

Such radial pins can be used as connection means or elements to reliably connect the cartridge assembly to the dispenser.

For example, the radial pins can be part of at least one of a bayonet type of connection and a plug and rotate type of connection. Such connections can be brought about and released in a fast and reliable manner.

The one or more radial pins can have the shape of a mushroom head in a sideview thereof. Radial pins having a head part and a cylindrical part can be beneficially used to connect the sleeve to a dispenser, as the guidance of such mushroom headed radial pin in a corresponding slot is improved.

It should be noted that the radial pins can be formed separate from the sleeve and can be retrospectively bonded to the sleeve, welded to the sleeve, screwed to the sleeve etc. after the single part sleeve is formed e.g. in an extrusion or casting process.

The one or more radial pins can be configured to connect the sleeve with counter elements present at the dispenser. In this way a fixation of the sleeve at the dispenser can be beneficially improved.

The sleeve can be of multi-part design. This means the sleeve can be formed of several parts, such as a front part and a rear part that can be connected to one another to form the sleeve, with the rear part comprising the radial pins which could be retrospectively added to the sleeve after the sleeve is formed.

The sleeve can comprise one or more joints, such as a threaded connection, a bayonet type of connection, a plug and rotate type of connection, for connecting the various parts of the sleeve one to another to form the sleeve. In this way e.g. the front part and the rear part of the sleeve can be releasably connected to one another in a reliable and fast way.

In this connection it is possible that the joint can be opened and closed in the same direction as the connection between the sleeve and the dispenser. Alternatively, it is possible that the joint is opened in the direction opposed to the direction of releasing the connection between the sleeve and the dispenser.

The sleeve can comprise metal and/or plastic. Such materials enable a quick and comparatively cheap manufacture of a sleeve having the required rigidity for the purpose of connecting the sleeve to the dispenser.

The sleeve can comprise an inner support sleeve and an outer sleeve. In this way the film bag cartridge can be protected in an improved way for insertion into the outer sleeve.

The inner support sleeve can be friction fit and/or press fit to the head part. By such a connection one can ensure that the support sleeve is fixed to the head part in order to reliably assemble the cartridge assembly.

The sleeve can comprise one or more retraction and/or catch mechanisms for the piston, for example the sleeve comprises at least one of the following, a cord via which the sleeve is connected to the piston and one or more crimps provided at an inner surface of the sleeve. By such retraction and/or catch mechanisms one can prevent the accidental loss of the piston which would render the cartridge assembly unusable.

The head part can have a dome-shaped outer shape, preferably the outlet projects from the dome-shaped part of the head part. An outwardly projecting dome shaped head part can be captively held by the part of the sleeve in a beneficial way and has an aesthetically pleasing shape. Alternatively, the head part can have a generally flat shape, optionally with the outlet projecting from the flat surface of the head part.

In this connection a dome shaped part means a part that gradually reduces in size between a maximum outer diameter and a minimum outer diameter, preferably via a curved surface.

The head part can have an end face, with the end face then having one of a dome-shaped outer shape and a flat shaped outer shape, with the end face of the flat shaped outer shape being adjoined by a sidewall extending between the end face and the collar, with the outlet in particular projecting from the end face of the dome shaped outer shape or the flat shaped outer shape respectively.

The part of the sleeve can cover the head part such that the head part cannot be moved in an axial direction relative to the sleeve when the head part is attached, in particular directly or indirectly, to the sleeve.

At least a part of the sidewall and/or at least some of the end face of the head part can optionally be covered by the part of the sleeve in order to maintain the fixed axial relationship between the head part and the sleeve.

The piston can have an outer shape that is formed complementary and sized complementary to an inner shape of the head part. In this way as much of the material as possible stored in the film bag cartridge can be dispensed from the film bag cartridge in order to reduce the amount of waste material present in a used film bag cartridge.

The piston can have a dome-shaped outer shape that is formed complementary to an inner and an outer shape of the head part. In this way the piston is beneficially formed complementary to a corresponding dome shaped head part.

According to a further aspect the present invention relates to system comprising a dispenser and a cartridge assembly filed with a material. Such a system can reliably be used for dispensing a plethora of materials in a fast and reliable manner.

The cartridge is thus filled with a material selected from the group of members consisting of topical medications, medical fluids, wound care fluids, cosmetic and/or skin care preparations, dental fluids, veterinary fluids, adhesive fluids, disinfectant fluids, protective fluids, paints and combinations of the foregoing.

Such fluids and hence the cartridge can therefore be expediently used in the treatment of target areas such as the nose (e.g. anti-histaminic creams etc.), ears, teeth (e.g. molds for implants or buccal applications (e.g. aphtas, gum treatment, mouth sores etc.), eyes (e.g. the precise deposition of drugs on eyelids (e.g. chalazion, infection, anti-inflammatory, antibiotics etc.), lips (e.g. herpes), mouth, skin (e.g. anti-fungal, dark spot, acne, warts, psoriasis, skin cancer treatment, tattoo removal drugs, wound healing, scar treatment, stain removal, anti-itch applications etc.), other dermatological applications (e.g. skin nails (for example anti-fungal applications, or strengthening formulas etc.) or cytological applications.

Alternatively, the fluids and hence the cartridge can also be used in an industrial sector both for the production of products as well as for the repair and maintenance of existing products, e.g. in the building industry, the automotive industry, the aerospace industry, in the energy sector, e.g. for wind-turbines, etc. The dispensing assembly can, for example, be used for the dispensing of construction material, sealants, bonding material, adhesives, paints, coatings and/or protective coatings.

In this connection it should be noted that the cartridge can be a one-component cartridge comprising only one cartridge chamber. Alternatively, the cartridge could be a two-component cartridge, such as a coaxial cartridge in which two chambers are arranged with a common axis, with a first of two chambers being arranged within a second of the two chambers.

According to a further aspect embodiments of the present invention relate to a sleeve, the sleeve comprising a front end having an opening for a cartridge outlet and a back end having one or more radial pins formed at an outer surface of the sleeve for connection to a dispenser, the sleeve further being configured to receive a film bag cartridge and the piston that cooperates with the film bag cartridge, wherein the sleeve is of multi-part design.

Such a sleeve can reliably be used for releasably connecting a film bag cartridge to a dispenser in a fast and reliable manner.

According to a further aspect an embodiment of the present invention relates to a method of assembling a system, the method comprising:
a. providing the film bag cartridge;
b. inserting the film bag cartridge into the sleeve and contacting the head part of the film bag cartridge to the part of the sleeve covering the solid head part;
c. aligning the one or more radial pins of the cartridge assembly with one or more slots of the dispenser;
d. moving the cartridge assembly along a longitudinal axis of the cartridge assembly towards the dispenser; and
e. rotating the one or more radial pins in the one or more slots to fix the cartridge assembly to the dispenser.

By way of such a method a film bag cartridge can be releasably connected to a dispenser in a fast and reliable manner.

BRIEF DESCRIPTION OF THE FIGURES

The invention will be explained in more detail hereinafter with reference to the drawings.

FIG. 5 is a sectional schematic view of the cartridge assembly of FIG. 4 installed in a dispenser;

FIG. 6 is a sectional view of a further cartridge assembly;

FIG. 7 is a sectional view of a further cartridge assembly;

FIG. 8 is a sectional view of the further cartridge assembly of FIG. 7, with a screw cap removed from the sleeve;

FIG. 9 is a sectional view of a further cartridge assembly;

FIG. 10 is a perspective view of a further cartridge assembly; and

FIG. 11 is a perspective view of yet a further cartridge assembly.

DETAILED DESCRIPTION

Figure 1:
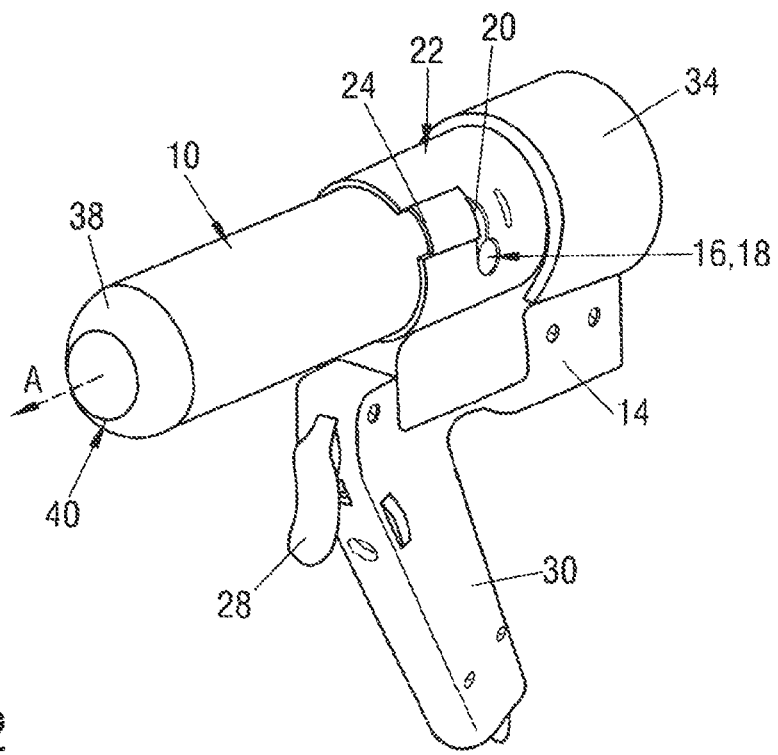
FIG. 1 is a perspective view of a sleeve of a cartridge assembly installed at a dispenser.

In the following the same reference numerals will be used for parts having the same or equivalent function. Any statements made having regard to the direction of a component are made relative to the position shown in the drawing and can naturally vary in the actual position of application.

FIG. 1 shows a perspective view of a sleeve 10 of a cartridge assembly 12 (see FIG. 4) installed at a dispenser 14.

The sleeve is attached to the dispenser 14 via a bayonet type of connection 16. For this purpose, the sleeve comprises two radial pins 18 and the dispenser comprises two matching female at least generally L-shaped slots 20.

The sleeve 10 is in fact inserted into a cartridge receptacle 22 of the dispenser 14. The cartridge receptacle 22 comprises two bridges 24 bridging a respective one of the limbs of the L-shaped slot 20. A height of the bridge is selected such that it is larger than a height the respective radial pin 18 projecting from the sleeve 10 such that the sleeve can be inserted into the cartridge receptacle 22.

The dispenser 14 further comprises an actuation mechanism 26 (see FIG. 5) which is configured to act on a piston 60 via a push plate 66 and a plunger 32 of the dispenser 14 (see also FIG. 5) for dispensing materials M stored in the cartridge assembly 12. In order to activate the actuation mechanism 26 a user pushes a trigger 28 present at a handle 30 of the dispenser 14.

As shown in FIG. 5, the push plate 66 and the plunger 32 are present in a rear end 34 of the dispenser 14. The rear end 34 is directly adjacent to the cartridge receptacle 22 such that the push plate 66 can be guided towards and into the sleeve 10 for moving the piston 60 along a longitudinal axis A of the dispenser 14 via the cartridge receptacle 22.

Figure 2:
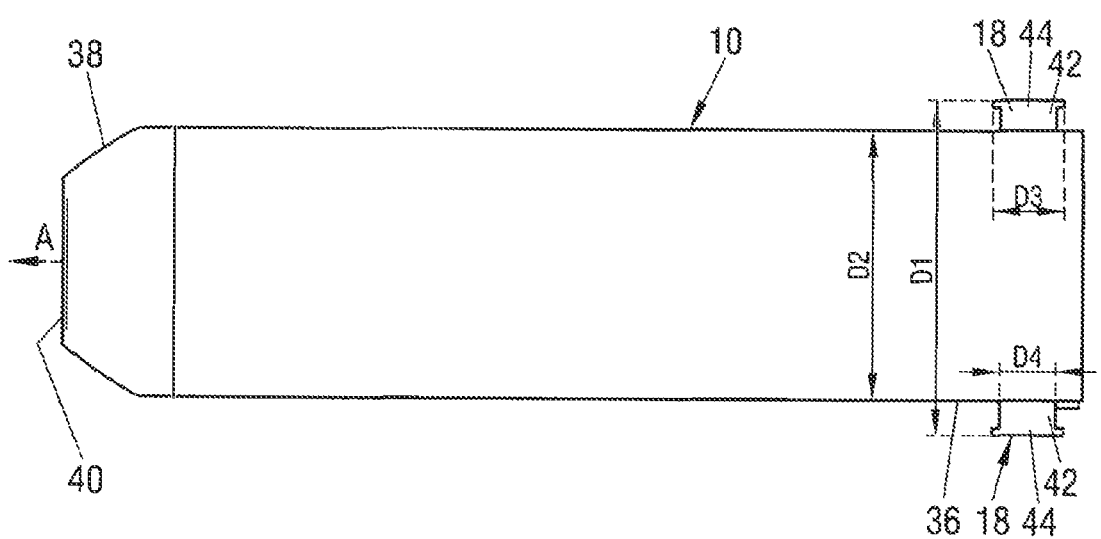
FIG. 2 is a sectional view of the sleeve of FIG. 1.

For this purpose, a back end 36 of the sleeve 10 is removably insertable into the cartridge receptacle 22. As shown in FIG. 2, the back end 36 comprises the radial pins 18 which in a sideview thereof comprise a cylindrical part 42 and a hat 44. Thereby the one or more radial pins 18 have the shape of a mushroom head in a sideview thereof. In this connection it should be noted that the bridges 24 are generally formed complementary in shape to the pins 18, in order to reliably guide the pins 18 in the slots 20.

The sleeve 10 has an outer diameter D1 at the radial pins of 55.4 mm. In this connection it should be noted that the outer diameter D1 can generally be selected in the range of 50 to 100 mm depending on the specific size of the cartridge assembly 12.

An outer diameter D2 at a region of the sleeve 10 directly adjacent to the radial pins 18 amounts to 45.4 mm. In this connection it should be noted that the outer diameter D2 of the sleeve 10 can generally be selected in the range of 40 to 95 mm.

A height of the pins 18 amounts to 5 mm. In this connection it should be noted that the height of the pins 18 can generally be selected in the range of 2.5 to 15 mm.

A diameter D3 of the hat 44 is 11.5 mm. In this connection it should be noted that the diameter D3 of the hat 44 can generally be selected in the range of 6.5 to 20 mm.

A diameter D4 of the cylindrical part 42 is 9 mm. In this connection it should be noted that the diameter D4 of the cylindrical part 42 can generally be selected in the range of 4 to 18 mm.

The sleeve 10 can be formed of a metal, such as stainless steel, aluminum or an aluminum alloy.

Alternatively, the sleeve 10 can be formed from a plastic, such as polyamide (PA), polypropylene (PP), or polyethylene terephthalate (PET), especially a plastic having a hardness measured on the Shore D scale selected in the range of 30 to 100. In this connection it should be noted that the PA, PP, or PET could be reinforced with natural fibers, such as wood and hemp.

Figure 3:
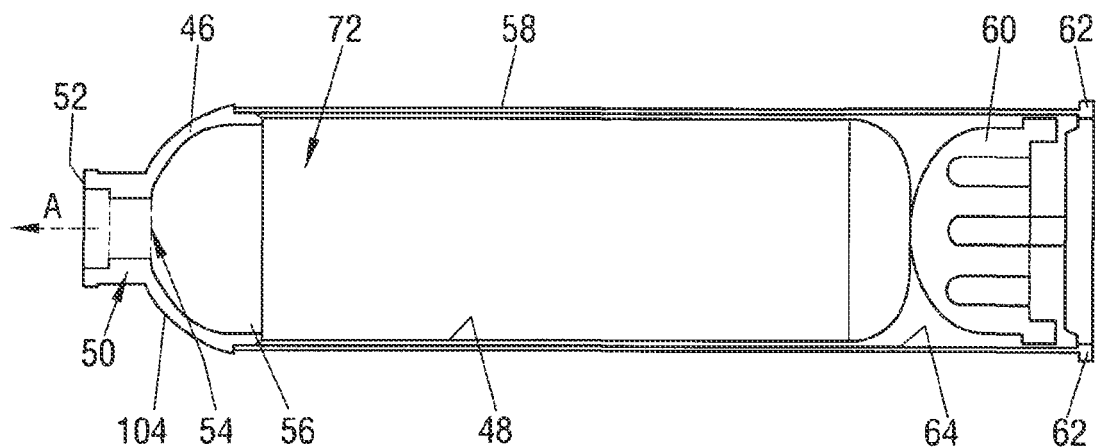
FIG. 3 is a sectional view similar to that of FIG. 2, with a film bag cartridge installed in a support sleeve.

As further shown in FIGS. 1 and 2 a front end 38 of the sleeve 10 comprises an aperture 40. The aperture 40 as shown e.g. in FIG. 3 is configured as an opening through which an outlet 50 having an outlet aperture 52 of the cartridge assembly 12 can be guided. The outlet 50 projects from the head part 46.

In this connection it should be noted that the aperture 40 has a diameter which is larger than a maximum outer diameter of the outlet 50, preferably wherein a diameter of the aperture 40 is selected as being between 105% and 250% of the maximum outer diameter of the outlet 50.

More specifically, the outlet 50 is disposed at a solid head part 46 of the cartridge assembly 12, with a film bag 48 being integrally formed at the head part 46 to form a film bag cartridge 72.

In this connection the head part 46 can have a Shore D hardness selected in the range of 40 to 99. Preferably the Shore D hardness of the head part can lie in the range of 40 to 60.

The head part 46 and/or the sleeve 10 can comprise polyethylene (PE), high density polyethylene (HDPE), polypropylene (PP), polyamide (PA), polyethylenterephthalate (PET) or polybutylenterephthalate (PBT). The head part 46 can for example comprise polyamide in the form of PA-6 (perlon) or PA-66 (nylon). Polyamide has the advantage that it has a good mechanical stability and is thus suitable for the head part 46.

One can also consider forming at least one of the sleeve 10 and the head part 46 of a material that has been recycled, for example recycled by 100%, such as HDPE, green PE (e.g. made of sugar cane) and PP.

Alternatively, the material of the head part 46 and/or of the sleeve 10 can comprise a compound which is formed by a mixture of green PE with normal PE, a mixture of green PE and recycled PE, or a mixture of normal PE with green PE and recycled PE. Also compounds comprising recycled PP, partially recycled PP and/or normal PP can be used in injection molding processes of the head part 46 and/or as the material of the cartridge wall. The use of such recycled materials leads to a more environmentally friendly cartridge 72.

The head part 46 and/or the sleeve 10 can additionally be reinforced with further material such as through the use of fibers, such as natural fibers, wood fibers, cellulose fibers, hemp fibers, cork fibers, fibers from sun flower seeds, grass fibers, bamboo fibers, flax or carbon fibers.

By way of example, PP, TPE, TPS can each be injection molded together with cork fibers. PE, PP, PLA, PBS, and/or PBAT can be used in injection molding processes together with wood or natural fibers. PA, PE and/or PP can be injection molded together with a wide range of natural fibers. PP and/or PE can be injection molded together with fibers from sun flower seeds. PE, PP, and/or PLA can be injection molded together with fibers grass fibers, flax. It is also possible to injection mold thermoplastic materials not only with one kind of fiber but a mixture of types of fibers.

Similarly it is possible to coat the cartridge 72, i.e. the head part 46 or the film bag 48 on the inside and/or on the outside with layers designed to improve the chemical capability of the cartridges, for example, to provide coatings that do not react with the contents stored in the cartridge 72, but which contents might react with materials of the cartridge walls, i.e. the film bag 48, or the head part 46.

Similarly, the coating materials could seal off the material of the head part 46 and/or of the film bag 48 in order to improve the long-term storage stability of the cartridge 72.

Using such coatings, the material of the head part 46 and/or of the film bag 48 forming the cartridge 72 does not inherently have to be suitable for the materials stored in the cartridge 72, i.e. one can manufacture a cost-effective cartridge 72 and subsequently coat this to make the cartridge 72 suitable for its then intended use.

Polyethylenterephthalats (PET) can also be used for the head part 46. PET can namely be processed in a facile manner and has a good chemical resistance.

In accordance with an embodiment the head part 46 is made of a high density PE (HDPE). High density polyethylene (HDPE) has a density in the range of 930 kg/m$^3$ to 970 kg/m$^3$ auf.

The film forming the film bag 48 can be a multilayer film having at least two layers formed from different materials. Alternatively, the film forming the film bag 48 can be a single layer film made of a single material.

For example, the film could be a three-layer film comprising a sandwich structure in which the first layer is formed of polyethylene (PE) (20 to 40 μm thickness), which is connected to a second layer of aluminum (Al) or of an aluminum alloy (Al alloy) (7 to 12 μm thickness) via a tie layer (1.5 to 2.5 μm thickness). The Al or AL alloy layer is in turn connected to a third PET layer (12 to 15 μm thickness) via a further tie layer (1.5 to 2.5 μm thickness).

For example, the film could be a four-layer film comprising a sandwich structure in which the first layer is formed of PE (20 to 40 μm thickness), which is connected to a second layer of aluminum (Al) or of an aluminum alloy (Al alloy) (7 to 12 μm thickness) via a tie layer (1.5 to 2.5 μm thickness). The Al or AL alloy layer is in turn connected to a third layer of PA (10 to 20 μm thickness) via a tie layer (1.5 to 2.5 μm thickness). The third layer of PA is in turn connected to a fourth layer of PE (15 to 30 μm thickness) via a further tie layer (1.5 to 2.5 μm thickness).

For example, the film could be a five-layer film comprising a sandwich structure in which the outer layer is formed of PE (20 to 40 μm thickness) which is connected to a layer of PA (10 to 20 μm) via a tie layer (1.5 to 2.5 μm). The PA layer in turn is connected via a further tie layer (1.5 to 2.5 μm) to an aluminum or aluminum alloy layer (5 to 10 μm). The aluminum or aluminum alloy layer is in turn connected to a further PA layer (10 to 20 μm) via a further tie layer (1.5 to 2.5 μm) which is then connected to an inner layer corresponding to the inner surface 42, via a via a further tie layer (1.5 to 2.5 μm) with the inner layer having a thickness selected in the range of 45 to 100 μm.

It should be noted that the respective tie layers are not considered to be individual layers of a multi-layered film, they are merely present to ensure a bond is formed between the individual layers.

The materials of the film can differ from the above mentioned materials as can their respective thicknesses. It should be noted in this connection that the multi-layered films typically have a thickness selected in the range of 40 to 200 μm, in particular of 50 to 170 μm.

A further film (not shown) can be provided at an inner surface 54 of the head part 46, with the same or a similar film to the film of the film bag 48 being selected as a material of the further film.

In this connection it should be noted that for so-called front filling operations, the further film covers the inner surface of the head part 46, but does not seal off the passage of the outlet 50, such that the material can be filled into the cartridge 72 via the outlet 50.

Alternatively, the further film can be arranged to cover a passage of the outlet 50, in these instances the cartridge 72 would typically be filled with material using the so-called back filling procedure in which the film bag 48 is open at its end opposite the head part 46 and the initially open end is sealed off after the filling procedure has been completed.

The film bag 48 is attached to a collar 56 of the head part 46. The collar 56 can have an outer diameter which is slightly smaller than the maximum outer diameter of the head part 46.

As shown in FIG. 3 the film bag 48 and the head part 46 are received in a support sleeve 58, as is the piston 60. The piston is moveable to and fro along an inner surface 64 of the support sleeve 58.

An first of the support sleeve 58 remote from the outlet 50 comprises a radially projecting abutment 62. The radial abutment 62 is configured as an end of the back end 36 of the sleeve 10 shown in FIG. 4 and projects as high as the outer diameter D2 of the outer sleeve 86 of the sleeve 10 shown in FIG. 4. The inner support sleeve 58 is slideably mounted within the outer sleeve 86 in order to permit a releasably assembly of the two components.

The sleeve 10 is thus of multi-part design. In this connection it should be noted that the support sleeve 58 can be formed of a plastic, such as a plastic described in the foregoing in relation to the materials of the head part 46. Specifically, the plastic of the support sleeve 58 can have a Shore D hardness selected in the range of 40 to 99. Preferably the Shore D hardness of the support sleeve can lie in the range of 40 to 60. The material of the outer sleeve 86 can then be selected as either the same plastic, a different plastic or a metal, such as aluminum, an aluminum alloy or stainless steel.

The inner support sleeve 58 can house the cartridge wall attached to the collar 56 of the head part 46, i.e. the inner support sleeve 58 covers the cartridge wall forming the film bag cartridge 72 in the region in which it is attached to the collar 56 in order to protect the film bag cartridge 72 in the region of the collar 56. This ensures a secure and reliable connection of the support sleeve 58 at the head part 46.

More specifically, a second end of the inner support sleeve 58 directly adjacent to the head part 46 and disposed opposite to the first end is connected to the collar 56 of the head part 46.

The provision of two or more cartridges 72 in a support sleeve 58 means that the time between changes of the cartridges 72 in a cartridge assembly 12 can be significantly reduced, which particularly for time sensitive applications, means that the cartridge 72 can be replaced quickly within the outer sleeve 86.

Figure 4:
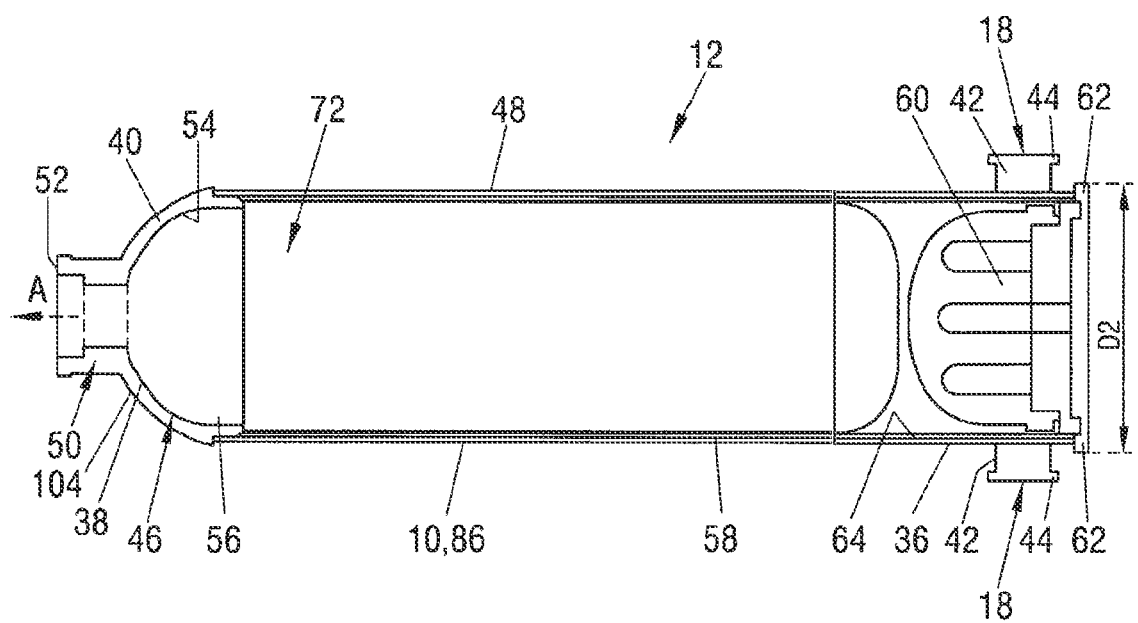
FIG. 4 is a sectional view of a cartridge assembly, with the film bag cartridge installed in the support sleeve of FIG. 3 installed in the sleeve of FIG. 2.

FIG. 4 shows a sectional view of the cartridge assembly 12, with a film bag cartridge 72 comprising the head part 46 and the film bag 48 installed in the support sleeve 58 of FIG. 3 installed in the sleeve 10, 86 of FIG. 2.

In this connection it should be noted that the inner support sleeve 58 can have a length selected in the range of 5 to 50 cm, in particular in the range of 10 to 40 cm and especially in the range of 12 to 20 cm.

It should further be noted that the inner support sleeve 58 can have a thickness selected in the range of 0.05 to 7 mm, in particular in the range of 0.25 to 3 mm and especially in the range of 0.5 to 2.5 mm.

In this connection it should be noted that the outer sleeve 86 can have a length selected in the range of 5 to 50 cm, in particular in the range of 10 to 40 cm and especially in the range of 12 to 20 cm.

It should further be noted that the outer sleeve 86 can have a thickness selected in the range of 0.05 to 7 mm, in particular in the range of 0.25 to 3 mm and especially in the range of 0.5 to 2.5 mm.

FIG. 5 shows a sectional schematic view of the cartridge assembly 12 of FIG. 4 installed in the dispenser 14. The dispenser 14 is a pneumatic dispenser having an air-line connector 68 for providing pressurizing air to the actuation mechanism 26 which has an air channel 70 therein for supplying pressurized air to the push plate 66 arranged at the back end 34 of the dispenser 14 for the purpose of dispensing. Such a system can reliably be used to dispense the materials M from the dispenser 14 in a fast and reliable manner. For this purpose a not shown nozzle can be connected to the outlet 50.

In this connection it should be noted that the nozzle can be connected to the outlet 50 by one of a threaded connection, a bayonet type connection or the like, with an inner and/or outer thread being present at the outlet 50 by way of example in dependence on the type of nozzle used.

In this connection it should be noted that the actuation mechanism 26 could also be formed by a manually operated mechanical actuation mechanism 26, a hydraulically driven actuation mechanism 26 and an electrically driven actuation mechanism 26.

FIG. 6 shows a sectional view of a further cartridge assembly 12. The cartridge 72 like the cartridge shown in the other Figures is a single component cartridge 72. The difference to the example shown in FIGS. 1 to 5 is that the sleeve 10 is of single part design and does not comprise a support sleeve 58.

FIG. 7 shows a sectional view of a further cartridge assembly 12. In order to connect the front part 76 of the sleeve to the rear part 78 of the sleeve, a threaded connection 74 is provided. In the examples shown in FIGS. 7 to 9 an inner thread 80 is present at the front part 76 and an outer thread 82 is present at the rear part 78. It should be noted in this connection that the outer thread 82 could also be present at the front part 76 and the inner thread 80 could then consequently be present at the rear part 78

In order to avoid the piston 60 from becoming lost on assembling the cartridge assembly 12, the sleeve 10 can comprises one or more retraction and/or catch mechanisms for the piston 60.

For example, the sleeve 10 can comprise a cord 84 via which the sleeve 10 is connected to the piston 60 as indicated in FIG. 7. Such a cord 84 can be present at any of the sleeves 10 shown in this description. This cord 84 enables the piston 60 to be held at the sleeve 10 with which it is associated.

The cord 84 also enables a user to retract the piston 60 from a forward position in which the piston 60 is closer to the head part 46 than it is to the back end 36, such that one can place a new cartridge 72 within the sleeve 10.

Similarly one or more crimps 88 can be provided at an inner surface 90 of the sleeve 10. Specifically with sleeves 10 as shown in FIGS. 7 to 9 it can be beneficial to have such crimps 88 present in the vicinity of the threaded connection 74, in particular arranged at the inner surface 90 of the sleeve 10 at the same position at which the outer thread 82 is provided. By way of such crimps 88 one can avoid the piston 60 from falling out of the sleeve 10 at the positions of the threaded connection 74.

Likewise crimps 88 can be provided at the inner surface 90 of the sleeve 10 at an axial height of the radial pins 18. In this way one can avoid the piston 60 from dropping out the back end 36 of the sleeve 10.

FIG. 8 shows a sectional view of the further cartridge assembly 12 of FIG. 7, with a screw cap 92 removed from the sleeve 10. On assembly of the cartridge assembly 12, the cartridge 72 is inserted in the rear part 78 and the film bag 48 is received within the sleeve 10, thereafter the screw cap 92 is screwed over the head part 46 and to the rear part 78 to form the cartridge assembly 12.

In this connection it should be noted that the front part 76 of the sleeve can have a length selected in the range of 0 to 20 cm, in particular in the range of 0 to 5 cm and especially in the range of 0.5 to 2.5 cm. In this connection it should be noted that 0 cm is the case for a flat front end with a threaded part only.

It should further be noted that the front part 76 of the sleeve can have a thickness selected in the range of 0.05 to 7 mm, in particular in the range of 0.25 to 3 mm and especially in the range of 0.2 to 3 mm, in regions where there is no part of the joint, such as the threaded connection 74.

In this connection it should be noted that the rear part 78 of the sleeve can have a length selected in the range of 5 to 50 cm, in particular in the range of 10 to 40 cm and especially in the range of 12 to 20 cm.

It should further be noted that the rear part 78 of the sleeve can have a thickness selected in the range of 0.05 to 7 mm, in particular in the range of 0.25 to 3 mm and especially in the range of 0.5 to 32.5 mm, in regions where there is no part of the joint, such as the threaded connection 74.

FIG. 10 shows a perspective view of a further cartridge assembly 12. Rather than using the screw cap 92, the cap includes a quick release fastener. This quick release fastener is present in the form of a bayonet closure, where radial pins 96 project from the sleeve 10 and cooperate with corresponding slots 98 present at the cap 92.

In this way the cap 92 can have a quick release fastener present thereat which cooperates with a corresponding member present at the sleeve 10 in order to reliably and quickly connect the cap 92 to the sleeve 10 in order to captively hold the head part 46 of the cartridge 72 at the sleeve 10.

The outer surface of the sleeve comprises a component 94 present thereat with the radially outwardly extending pins 96 projecting from the separate component 94. The separate component 94 can be formed from the same or a different material as the sleeve 10. The separate component 94 is directly connected to the outer surface of the sleeve 10.

In a non-shown design the pins 96 can be formed directly at the outer surface of the sleeve 10 from the same material as the sleeve 10 or from a different material than the material of the sleeve 10 and then project radially outwardly from the sleeve 10.

It should also be noted that the pins can be provided at the cap 92 and mate with two or more slots (not shown) present at the sleeve 10, in this instance the pins would then project radially inwardly.

FIG. 11 shows a perspective view of yet a further cartridge assembly 12. In this instance a screw cap 92 is used but this is fastened to the separate component 94 which then has an outer thread 82 present at an outer surface thereof. The separate component 94 is then directly connected to the outer surface of the sleeve 10. The separate component 94 shown in FIG. 11 can also be formed from the same or a different material as the sleeve 10 of FIG. 11.

In this connection it should be noted that a seal can be present between the sleeve and the cap and/or the screw cap in order to provide a barrier at this point of connection between the sleeve 10 and the cap 92 shown in the FIGS. 7 to 11. Such sealing elements can be required, if a gas driven dispenser is used to drive the material out of the cartridge, either directly or indirectly via the piston 60.

In this connection it should be noted that if a gas driven dispenser is used then the sleeve 10 can also comprise sealing elements (not shown) at its back end 36, in order to allow a pressure chamber to be formed within the sleeve 10.

In this connection it should further be noted that the connectors, i.e. the outer thread, slots and/or radial pins, optionally present at the outer surface of the sleeve 10 as shown in FIGS. 10 and 11 are provided at the component 94 that is separate from the sleeve 10.

The component separate 94 from the sleeve 10 if used can then be press fit and/or friction fit and/or snap fit and/or adhesively bonded, and/or welded into place at the sleeve 10 in the form of an outer sleeve or ring. The component 94 separate from the sleeve 10 then cooperates directly with the cap 92 and the sleeve 10. In the designs shown in FIGS. 7 to 9, the cap 92 interacts directly with the sleeve 10.

The use of such separate components 92 can become necessary for manufacturing reasons, but a single piece sleeve 10 having the connectors directly present thereat is also highly desirable for certain applications.

As also indicated in FIGS. 10 and 11 the sleeve 10 can comprise one or more through bores and/or apertures 100 at a pre-defined axial height (not shown). These apertures 100 can be provided if the dispenser 14 is a gas driven dispenser 14 in which the piston 60 is moved by gas and not by a push rod. These apertures 100 then prevent the piston 60 from moving too far axially forward in the direction of the head part 46 beyond a pre-defined position, i.e. to prevent the piston 60 from getting stuck at the head part 46 and/or the front end 38 of the sleeve and/or from even dropping out the end of the front end 38 of the sleeve 10. This is because the apertures 100 are designed to release the pressure present in the sleeve 10 at this pre-defined position.

On the outer surface of the sleeve 10 there can be one or more recesses 102 which connect with the one or more apertures 100 in order to ensure a connection between the apertures 100 and the atmosphere.

Generally speaking the piston 60 has an outer shape that is formed complementary to an inner shape of the head part 46. This is done to ensure as much of the material M stored in the respective cartridge 72 as possible can be dispensed from the cartridge 72.

In this connection it should be noted that the head part 46 of the cartridges 72 shown in FIGS. 2 to 8 each have a dome-shaped outer shape. This shape is mirrored in the dome shaped front ends 38 of the respective sleeve 10. The piston 60 consequently also has a dome-shaped outer shape that is formed complementary to the inner and the outer shape of the head part 46.

FIG. 9 shows a sectional view of a further cartridge assembly 12. The difference to the examples shown in the foregoing is that the front end 38 of the sleeve 10 like the head part 46 has an at least substantially flat shape from which the outlet 50 projects. Like the example shown in FIGS. 7 and 8 the sleeve 10 is a two-part sleeve, with the front and rear parts 76, 78 being connected via the threaded connection 74.

Regarding the designs with a dome shaped outer and a flat shaped outer shape, both have end faces 104 with the end faces 104 being covered by the part of the sleeve.

As indicated in FIGS. 9 to 11 the end face 104 having the flat shaped outer shape is directly adjoined by a sidewall 106 extending between the end face 104 and the collar 56.

The outlet 50 can project from the end face 104 of the dome shaped outer shape or the flat shaped outer shape respectively.

In a non-illustrated design the sleeve 10 can comprise bayonet type slots at its front end 38 which mate with radial pins provided at the sidewall 104 of the head part, so that the head part 46 directly locks into the sleeve 10 via this bayonet type of connection. In this instance the sleeve 10 then covers the sidewall 106 of the head part 46.

In all of the embodiments shown the sleeve 10 comprises a part that covers a part of the head part 46 in order to captively hold the front end 38 of the sleeve 10 on dispensing materials M from the cartridge assembly. This becomes necessary as the dispenser depicted in FIGS. 1 and 5 does not comprise a cartridge receptacle in which the front end 38 of the cartridge 72 is held. Rather the cartridge assembly 12 is only held at the dispenser via the pins 18 interacting with the slots 20.

In this connection it should be noted that the part of the sleeve 10 that covers the head part can cover between 10 to 80%, in particular 25 to 65%, of the head part 46. In particular it should be noted that the part of the sleeve 10 that covers the head part 46 can cover between 10 to 80%, in particular 25 to 65%, of the end face 104 of the head part 46.

In this connection it should be noted that the end face 104 is that part of the head part 46 that projects away from the film bag cartridge 72 along the longitudinal axis A and that is remote from any material M stored in the cartridge 12 when the cartridge 12 is not in use.

In this connection it should be noted that a maximum outer diameter of the outlet 50 can be selected in the range of 6 to 25 mm. Depending on the specific outer maximum diameter of the outlet 50, an inner diameter of the aperture 40 is selected larger than this maximum diameter such that the outlet 50 can pass through the aperture 40. The aperture can have a minimum inner diameter selected in the range of 10 to 30 mm, preferably wherein the aperture 40 has an inner diameter that is selected 30 to 300% (i.e. 1.3 to 3 times as large) larger than a maximum outer diameter of the outlet 50.

In order to assemble the system comprising the cartridge 72 and the dispenser 14, the following steps have to be carried out:
a. providing the film bag cartridge 72;
b. inserting the film bag cartridge 72 into the sleeve 10 and contacting the head part 46 of the film bag cartridge 72 to the part of the sleeve 10 covering the solid head part 46 to form a cartridge assembly 12;
c. aligning the one or more radial pins 18 of the cartridge assembly 12 with one or more slots 20 of the dispenser 14;
d. moving the cartridge assembly 12 along the longitudinal axis A of the cartridge assembly 12 towards the dispenser 14; and
e. rotating the one or more radial pins 18 in the one or more slots 20 to fix the cartridge assembly 12 to the dispenser 14.

The invention claimed is:

1. A cartridge assembly comprising:
a film bag cartridge;
a sleeve; and
a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design,
the sleeve comprising an inner support sleeve and an outer sleeve.

2. The cartridge assembly in accordance with claim 1, wherein the one or more radial pins have the shape of a mushroom head.

3. The cartridge assembly in accordance with claim 1, wherein the one or more radial pins are configured to connect the sleeve to cooperate with counter elements present at the dispenser.

4. The cartridge assembly in accordance with claim 1, wherein the sleeve comprises one or more joints to connect parts of the sleeve to one another to form the sleeve.

5. The cartridge assembly in accordance with claim 1, wherein the sleeve comprises at least one of metal and plastic.

6. The cartridge assembly in accordance with claim 1, wherein the inner support sleeve is friction fit or press fit to the head part or the inner support sleeve is slideably mounted within the outer sleeve.

7. The cartridge assembly in accordance with claim 1, wherein the head part has an end face, with the end face having one of a dome-shaped outer shape and a flat shaped outer shape.

8. The cartridge assembly in accordance with claim 7, wherein an outlet projects from the end face.

9. The cartridge assembly in accordance with claim 1, wherein the inner support sleeve houses the cartridge wall attached to a collar of the head part.

10. The cartridge assembly in accordance with claim 1, wherein the piston has a dome-shaped outer shape that is complementary to an inner and an outer shape of the head part.

11. A system comprising:
a dispenser; and
the cartridge assembly in accordance with claim 1 filed with a material.

12. A method of assembling a system in accordance with claim 11, the method comprising:
providing the film bag cartridge;
inserting the film bag cartridge into the sleeve and contacting the head part of the film bag cartridge to the part of the sleeve covering the solid head part to form the cartridge assembly;
aligning the one or more radial pins of the cartridge assembly with one or more slots of the dispenser;
moving the cartridge assembly along a longitudinal axis of the cartridge assembly towards the dispenser; and
rotating the one or more radial pins in the one or more slots to fix the cartridge assembly to the dispenser.

13. A cartridge assembly, comprising:
a film bag cartridge;
a sleeve; and
a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design,
the sleeve comprising one or more retraction or catch mechanisms for the piston.

14. A cartridge assembly, comprising:
a film bag cartridge;
a sleeve; and
a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design, the head part having an end face, with the end face having one of a dome-shaped outer shape and a flat shaped outer shape, and the cartridge wall formed by the film being integrally formed at a collar of the head part.

15. A cartridge assembly, comprising:

a film bag cartridge;

a sleeve; and a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design, the part of the sleeve covering the head part such that the head part is incapable of moving in an axial direction relative to the sleeve when the head part is attached to the sleeve.

16. A cartridge assembly, comprising:

a film bag cartridge;

a sleeve; and a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design, at least a part of a sidewall or at least some of an end face of the head part covered by the part of the sleeve.

17. A cartridge assembly, comprising:

a film bag cartridge;

a sleeve; and a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design, the sleeve comprising at least one of the following, a cord via which the sleeve is configured to be connected to the piston or one or more crimps at an inner surface of the sleeve.

18. A cartridge assembly, comprising:

a film bag cartridge;

a sleeve; and a piston, the film bag cartridge having a solid head part and a cartridge wall formed by a film integrally formed with the head part, the film bag cartridge and the piston being received in the sleeve, a part of the sleeve covering a part of the solid head part and the sleeve comprising one or more radial pins that are arranged at an end of the sleeve remote to the head part to connect the sleeve to a dispenser, the sleeve being a multi-part design, the head part having an end face, with the end face having one of a dome-shaped outer shape and a flat shaped outer shape with an outlet projecting therefrom, and when the end face has the flat outer shape the end face is adjoined by a sidewall extending between the end face and the collar, and when the end face has the dome-shaped outer shape.

* * * * *